United States Patent
Minambres Rodriguez et al.

(12)

(10) Patent No.: US 6,251,655 B1
(45) Date of Patent: Jun. 26, 2001

(54) **PROCESS FOR INCREASING THE PRODUCTION OF PENICILLIN G (BENZYLPENICILLIN) IN *PENICILLIUM CHRYSOGENUM* BY EXPRESSION OF THE PCL GENE**

(75) Inventors: Baltasar Minambres Rodriguez; Honorina Martinez Blanco; Elias Rodriguez Olivera; Belen Garcia Alonso, all of Leon; Jose Manuel Fernandez Canon, Madrid; Jose Luis Barredo Fuente, Leon; Bruno Diez Garcia, Leon; Carmen Schleissner Sanchez, Leon; Miguel Angel Moreno Valle, Leon; Francisco Salto Maldonado, Madrid; Jose Maria Luengo Rodriguez, Leon, all of (ES)

(73) Assignee: Antibioticos S.A., Madrid (ES)

( * ) Notice: Subject to any disclaimer, the term of this patent is extended or adjusted under 35 U.S.C. 154(b) by 0 days.

(21) Appl. No.: 08/952,457

(22) PCT Filed: Mar. 18, 1997

(86) PCT No.: PCT/ES97/00069

§ 371 Date: Oct. 28, 1998

§ 102(e) Date: Oct. 28, 1998

(87) PCT Pub. No.: WO97/35013

PCT Pub. Date: Sep. 25, 1997

(30) Foreign Application Priority Data

Mar. 18, 1997 (ES) .................................................. P9600664

(51) Int. Cl.[7] .............................. C12N 1/20; C12N 9/00; C12P 37/00; C07H 21/04

(52) U.S. Cl. .................. 435/252.3; 435/43; 435/183; 435/320.1; 536/23.2; 530/350

(58) Field of Search ................................ 435/183, 252.3, 435/320.1, 43; 536/23.2; 530/350

(56) References Cited

FOREIGN PATENT DOCUMENTS 9207079  4/1992  (WO).
9702349  1/1997  (WO).

OTHER PUBLICATIONS

Martinez–Blanco, H. Et al. "Purification and Biochemical Characterization of Phenylacetyl–CoA Ligase from Pseudomonas putida." Journal of Biological Chemistry, vol. 265, No. 12 (Apr. 1990), pp. 7084–7090.

Martinez–Blanco, H. Et al. ""In Vitro" Synthesis of Different Naturally–Occurring, Semisynthetic and Synthetic Penicillins Using a New and Effective Enzymatic Coupled System." Journal of Antibiotics, vol. 44, No. 11 (Nov. 1991), pp. 1252–1258.

Martinez–Blanco, H. Et al. "Design of an enzymatic hybrid system: a useful strategy for the biosynthesis of benzylpenicillin in vitro." FEMS Microbiology Letters, vol. 72, (1990), pp. 113–116.

ES 2033590 Antibioticos, S.A. (Mar. 16, 1993).

Martinez–Blanco, H. Et al. "Characterisation of the gene encoding acetyl–CoA synthetase in Penicillium chrysogenum: conservation of intron position in plectomycetes." Gene, vol. 130 (1993) pp. 265–270.

Ferrero, O. Et al. "Synthesis of 3–furylmethylpenicillin using an enzymatic procedure." FEMS Microbiology Letters, vol. 83 (1991).

Minambres, B. Et al. "Molecular Cloning and Expression in Different Microbes of the DNA Encoding Pseudomonas putida U Phenylacetyl–CoA Ligase." Journal of Biological Chemistry, vol. 271, No.52 (Dec. 27, 1996), pp. 33531–33538.

*Primary Examiner*—Ponnathapu Achutamurthy
*Assistant Examiner*—Tekchand Saidha
(74) *Attorney, Agent, or Firm*—Ladas & Parry

(57) ABSTRACT

An isolated DNA encoding phenyl acetyl-CoA-ligase and a process of increasing the production of penicillin G in a strain of *Penicillium chrysogenum* by transforming the strain with the isolated DNA. Also vectors and host organisms having the isolated DNA.

12 Claims, 5 Drawing Sheets pLStu
(4.77 Kb)

pALPs9
(9.0 Kb)

PROCESS FOR INCREASING THE PRODUCTION OF PENICILLIN G (BENZYLPENICILLIN) IN *PENICILLIUM CHRYSOGENUM* BY EXPRESSION OF THE PCL GENE

FIELD OF THE INVENTION

This invention describes a new process for obtaining strains of *Penicillium chrysogenum* with greater penicillin G production capacity, by the introduction and expression in the control strain of an exogenous gene which codes for the enzyme phenylacetyl-CoA ligase and which originates from the bacterium *Pseudomonas putida*.

PRIOR ART

Figure 1:
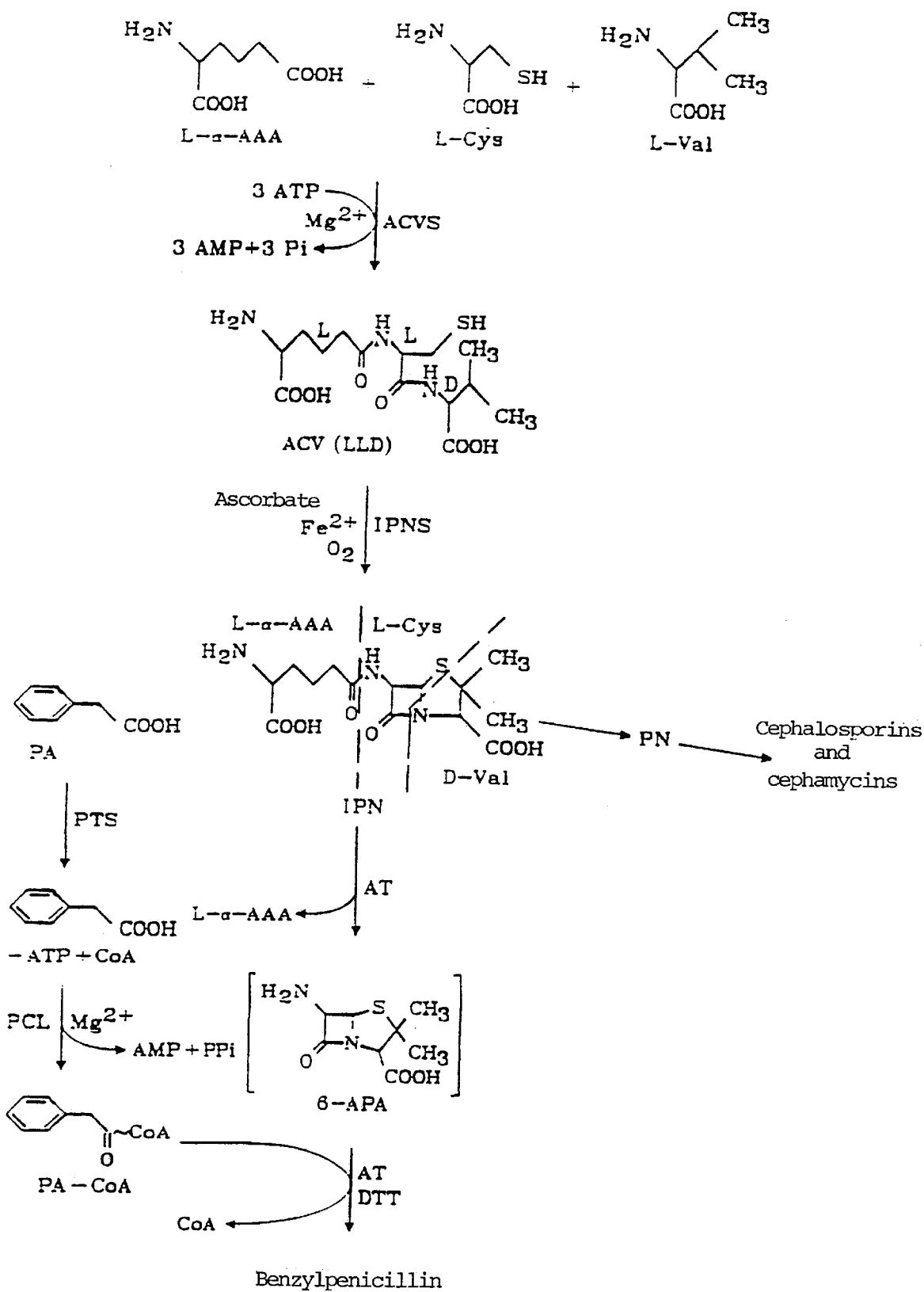

The pathway for biosynthesis of benzylpenicillin (penicillin G) in *Penicillium chrysogenum* is a linear and branched metabolic pathway which leads on one side to the amino acid L-lysine and on the other to the said antibiotic (see FIG. 1).

The penicillins-specific branch begins with the non-ribosomal condensation of three amino acids (L-α-aminoadipic, L-cysteine and L-valine), giving rise to a linear tripeptide (L-α-aminoadipyl-L-cysteinyl-D-valine), also called ACV, which lacks antibacterial activity (Ref. 1). The enzyme which catalyses this conversion is L-α-aminoadipyl-L-cysteinyl-D-valine synthetase, which in abbreviated form is called ACVS (Ref. 2). In a subsequent step the tripeptide ACV is converted to isopenicillin N (IPN) by the cyclization of the L-cysteine and D-valine residues (Ref. 3). This reaction leads to the synthesis of a molecule which has two rings, β-lactam and thiazole, and in which the remainder of the L-α-aminoadipic acid remains as a side chain (FIG. 1, Ref. 3). IPN is the first molecule in the pathway which has antibacterial activity, although its potency against G-organisms is poor. The enzyme responsible for synthesis of this compound is isopenicillin N synthetase (IPNS) (Ref. 3). In a subsequent stage (see FIG. 1) *Penicillium chrysogenum* replaces the remainder of the L-α-aminoadipic acid present in the IPN with phenylacetic acid, giving rise to a molecule which keeps the β-lactam and thiazole rings but which now has phenylacetic acid as a side chain. This penicillin, called penicillin G or benzylpenicillin, has a greater potency than IPN and a much broader antibacterial spectrum.

The final stage of penicillin G biosynthesis requires at least three different enzymatic reactions. First, the phenylacetic acid has to be incorporated from the culture medium into the cell. This step is catalyzes by a specific transport system referred to by the abbreviation PTS (FIG. 1) (Ref. 4). Next, the phenylacetic acid is activated to phenylacetyl-CoA (PA-CoA) by a mechanism, not well known, which appears to require the involvement of a phenylacetyl-CoA-ligase (PCL). Finally, the PA-COA is used by the enzyme acyl-CoA:6-aminopenicillanic acid (isopenicillin N) acyltransferase (AT) (Ref. 5), in such a way that this protein catalyzes the acylation of the 6-amino group of the 6-aminopenicillanic acid (6-APA) or else the interchange between the remainder of the L-α-aminoadipic acid present in the IPN molecule and phenylacetyl-CoA, releasing the products penicillin G and CoA in the first case (when the substrates are 6-APA and phenylacetyl-CoA) and penicillin G, CoA and L-α-aminoadipic acid in the second case (when the substrates are IPN and PA-COA) (Ref. 6).

The biochemical and genetic studies carried out to date (Ref. 5) have allowed all he enzymes of the penicillin G specific biosynthetic pathway to be identified and their genes to be characterized, with the exception of the enzyme phenylacetyl-CoA ligase, which it has not been possible to purify and the gene of which is unknown at the moment. In addition, the amounts of the different biosynthetic enzymes (ACVS, IPNS and AT) detected in different strains of *Penicillium chrysogenum* (both in those whose production of penicillin G is low and in other strains used industrially) are sufficiently high to eliminate the possibility of any of them being considered a limiting stage in the biosynthesis of penicillin G (Ref. 7–8). For this reason a study was commenced of the enzyme phenylacetyl-CoA ligase (PCL), the only enzyme in the pathway for which the sequence is not fully known. The absence of detectable amounts of enzyme in all the strains of *Penicillium chrysogenum* studied means that different microorganisms have to be selected for their ability to grow in a medium of defined composition (minimal medium, MM) containing phenylacetic acid (PA) as the sole carbon source (Ref. 9), and also that the existence of phenylacetyl-CoA ligase activity has to be assessed in all the selected strains. Of all the microorganisms isolated, a strain of *Pseudomonas putida* U was selected which breaks down phenylacetic acid aerobically by means of an undescribed degradation pathway involving a new enzyme: phenylacetyl-CoA ligase (EC 6.2.1.30). This enzyme was purified to homogeneity and characterized biochemically (Ref. 9). The *Pseudomonas putida* U enzyme, which we will hereinafter call PLC, presents some optimal physicochemical conditions which are very similar to the IPNS and AT of *Penicillium chrysogenum*, and so it was thought that the three enzymes could work together in vitro. It was shown that the PCL of *Pseudomonas putida* U and the IPNS and AT of *Penicillium chrysogenum* could be linked in vitro and used in this form for the production of both penicillin G and other penicillins in the laboratory (Ref. 10). These results, which are described in Spanish Patents Nos. P8902421 and 2016476 A6, allowed the possibility to be suggested that the PCL of *Pseudomonas putida* U might be expressed in *Penicillium chrysogenum* and that, if this enzyme was a limiting stage in the biosynthetic pathway, greater production of penicillin G might be achieved.

DESCRIPTION OF THE INVENTION

1. Isolation of the gene which codes for the enzyme phenylacetyl-CoA ligase in *Pseudomonas putida* U The strain of *Pseudomonas putida* U, which had phenylacetyl-CoA ligase activity when grown in the MM described in Ref. 9, was mutated by the insertion of the transposon Tn5 (Ref. 11), as is detailed in the protocol shown in FIG. 2. The strains which were unable to break down phenylacetic acid were selected, which suggested that the insertion had occurred in one of the genes, or intergenic regions, corresponding to the catabolic pathway of this aromatic compound. In all the mutants PCL activity was assayed as described in Spanish Patent P8902421 and in the corresponding publication (Ref. 9). For this purpose the various mutants were grown in the same MM, but it now contained, as carbon sources, 4-hydroxyphenylacetic acid (4-OHPA), which does not induce PCL, and phenylacetic acid (PA), which, although it cannot be broken down, could induce PCL (Ref. 12). In this MM the 4-OHPA is used by the bacteria to sustain cell growth whereas the PA acts as an inducer of the enzyme phenylacetyl-CoA ligase.

By this simple procedure the various mutants were characterized in such a way that two groups could be established:

a) those which possessed functional PCL (called PCL+) and in which the transposon Tn5 had thus inserted itself into a gene on the pathway (or into an intergenic region) after the gene coding for PCL, and b) the others in which this activity could not be detected (called PCL−).

The absence of PCL in this second group of mutants could be due to two reasons:

1) it could be due to the fact that the transposon had inserted itself in front of the gene coding for the ligase (pcl) (if, as was suspected, all the catabolic pathway responsible for the breakdown of PA is under the control of one promoter), or it could be due to the fact that 2) the Tn5 had incorporated itself into the pcl gene itself, or into a regulator gene or sequence.

From one of the mutants in which no PCL activity was detected, called $E_1$, the insertion of Tn5 was identified by the use of oligonucleotide sequences which were exactly the same as the ends of Tn5 (5' D 3': ACT TGT GTA TAA GAG TCA G SEQ ID NO:13) and which had been radioactively labelled. The zone of the $E_1$ mutant genome linked to the transposon was cloned in the plasmid pUC 18 and the *Escherichia coli* strain D5α' was transformed in accordance with the conventional protocols (Ref. 13). The insert was then sequenced and the gene which hybridized with the gene sequence isolated from the mutant $E_1$, and which corresponded to the adjacent zone of the transposon, was searched for in a *Pseudomonas putida* U DNA library produced in the phage λ EMBL4. Of all the phages which gave positive hybridization, three which contained 13, 15 and 18 Kb fragments of the genomic DNA of *Pseudomonas putida* were selected. From one of these, the one which contained a 13 Kb insert, DNA was extracted (Ref. 13), it was cleaved with the restriction enzyme EcoRI, and a 10 Kb fragment was selected. When this fragment of *Escherichia coli* DH5α' was introduced, using the plasmid pUC 18 as transformation vector, the presence of the insert gave the latter bacterium the ability to grow in MM which contained PA as the sole carbon source. Growth was slower, however, than that observed in *Pseudomonas putida* U—which suggested that although it contained genes which made catabolism of this compound possible, its breakdown rate in *Escherichia coli* was much slower. This effect could be due either to the fact that (i) a gene (or genes) needed for total breakdown of PA is (are) missing or incomplete in the fragment—which would force the bacterium to replace it (them) with another one (or others) present in its own genome, so as to allow it to use the accumulated catabolite, albeit more slowly; or to the fact that (ii) despite all the required genes being present in the fragment, the toxicity caused by PA (or by one of its breakdown products) prevented more effective utilization of this compound in *Escherichia coli*. In addition, it was shown that those bacteria (*Escherichia coli* DH5α') which did not contain the plasmid pUC 18+insert, or others which only had the plasmid pUC 18 without the 10 Kb insert, were unable to grow in MM+PA as sole carbon source—which clearly demonstrates that (i) the catabolism of phenylacetic acid was essentially due to the expression of the genes included in the 10 Kb fragment and (ii) the *Escherichia coli* strain used (DH5α') did not have any functional enzymes enabling it to grow in MMs which contained PA as the sole carbon source. It was subsequently confirmed that this fragment contained the pcl gene, as considerable phenylacetyl-CoA ligase activity was detected in cell-free extracts of *Escherichia coli* DH5α', whereas not even basal levels of the said activity were detected in the same bacteria without pUC 18+insert, or in others which only had pUC 18.

Figure 3:
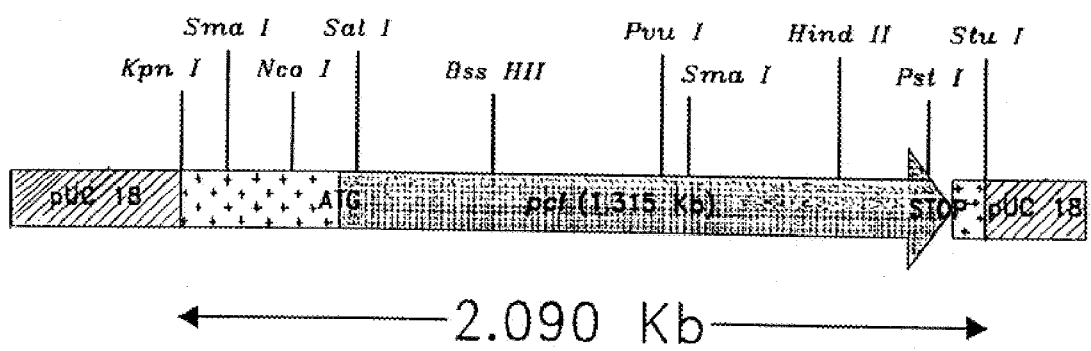

Subsequent studies allowed a more discrete fragment (2090 base pairs) to be obtained which, cloned in pUC 18, coded for a protein with PCL activity, and the restriction analysis of which is given in detail in FIG. 3. The nucleotide sequence of the pcl gene was called SEQ ID NO:1.

The amino acid sequence of the protein coded for by this gene was called SEQ ID NO:2. The determination of ligase activity was carried out as described in Ref. 9, but now starting with cell-free extracts of *Escherichia coli* which had grown in LB medium (see Luria-Bertani in Ref. 13), supplemented with 100 μg/ml of the antibiotic ampicillin (in those cases where cells containing the gene which coded for the β-lactamase present in the plasmid pUC 18 were being analyzed) or in the absence of the antibiotic, if the cells did not contain the plasmid. In all cases the bacteria were collected when the absorbance ($Abs_{540\ nm}$) of the culture diluted 1/10 was 0.2. Under these conditions the proportion of PCL present in the extracts free of those cells which contained the insert carrying the pcl gene was 23% relative to total protein. All the oligopeptides obtained by analysis of the amino terminal of the protein previously purified from *Pseudomonas putida* U were found in this sequence, as well as the others obtained by tryptic digestion of the same enzyme. This protein presents a consensus sequence (SSGTTGKP SEQ ID NO:14) which corresponds to an AMP binding site (Ref. 14–15). In addition, the enzyme was purified from the *Escherichia coli* DH5α' strain which had been transformed with pUC 18+the insert indicated in FIG. 3, it being possible to show that: (i) the protein expressed had the same molecular weight as that obtained from *Pseudomonas putida* U; and (ii) that this enzyme could also be linked to the IPNS and AT of *Penicillium chrysogenum*, giving in vitro synthesis of penicillin G.

When expression in *Escherichia coli* DH5α' using the plasmid pUC 19 as vector was employed, however, PCL activity was not detected—which suggests either that the *Pseudomonas putida* U promoters are not expressed in *Escherichia coli* or that there are no promoter sequences in the DNA fragment available.

Subsequent studies carried out to shorten the fragment shown in FIG. 3 by digesting it with the enzymes exonuclease III/nuclease S1 (using the Erase-a-base system supplied by the PROMEGA company) (Ref. 16) allowed a clone Bal116 (SEQ ID NO: 8) to be obtained which had lost a sequence fragment (in front of the one coding for PCL) but which, however, kept the same amino terminal sequence as the PCL purified from *Pseudomonas putida* U (MNMYH). Analysis of the different gene sequences obtained when the fragment of 2090 base pairs was digested with exonuclease III/nuclease Si (Erase-a-base system) (Ref. 16) for different periods of time suggested that the expression of these DNA fragments in *Escherichia coli* could lead to different PCLs in which only the amino terminal sequence changed. Analysis of the PCL activity expressed in *Escherichia coli* (TABLE I) revealed that the amino terminal end of the native protein (MNMYH), corresponding both to that purified from *Pseudomonas putida* U and to that encoded by the clone Bal116, could change without any appreciable variation in enzymatic activity. Thus, the clone Bal112 (SEQ ID NO: 7), which codes for a PCL with a longer amino terminal end (MTMITNSSNSSEAMNM SEQ ID NO:15), kept the same activity as that expressed from the clone Bal116. The same happened when a study was made of the activity of the proteins expressed by the clones Bal142 (SEQ ID NO: 10) and Bal101 (SEQ ID NO: 3), the amino terminals of which had been considerably reduced (MTMITNSRYH (SEQ ID NO:16) and MTMITNSSDA (SEQ ID NO:17), respectively). From the clone Bal110 (SEQ ID NO: 6) a protein was obtained the amino terminal of which (MTMITNSSWRAAYKNNSSEAMNMYH SEQ ID NO:18) was longer than that encoded by the construct corresponding to Bal112 due to the presence of an internal WRAAYKN (SEQ ID NO:19) sequence. This protein did not exhibit any PCL activity—which shows that although it is possible to introduce certain modifications into the amino terminal end of the protein without changing the activity, others, such as the one described, lead to non-functional enzymes in spite of keeping the complete sequence of the native protein. This result is particularly interesting as it shows that, provided that the MTM sequence belonging to the pUC 18 polylinker exists, the PCL cloned in *Escherichia coil* is not expressed from its own ATG. With the aim of establishing the importance of the two methionines present in the polylinker (MTM) use was made of a variant of pUC 18 in which a deletion of one of the two cytosines located between the two ATGs of the plasmid had occurred and which consequently gave rise to a STOP signal. The sequence in this mutated plasmid is called SEQ ID NO: 11. The loss of this C produces a reading frame shift such that the protein would only be able to start in the second methionine. Using this vector a study was made of the expression of a construct which did not have any of the nucleotide sequences coding for the two methionines present in the amino terminal end of the native PCL, which is the case with the construct Bal142. Analysis of the PCL expressed revealed that a functional protein was produced, showing that the second ATG of the polylinker marks the beginning of the PCL cloned.

In those other constructs, created in the original plasmid zUC 18, in which there were stop signals in the three reading frames, the different PCLs start to synthesize from the amino terminal of the native protein (this is the case with the clones Bal106—SEQ ID NO: 4-, Bal107—SEQ ID NO: 5-, Bal116 and Bal117—SEQ ID NO; 9-).

All these data allowed the conclusions to be drawn that:
a) the gene cloned corresponds to the one which codes for the enzyme PCL in *Pseudomonas putida* U
b) the expression of this protein in *Escherichia coli* DH5α' is governed by the promoter of β-galactosidase present in the plasmid pUC 18, and that
c) discrete modifications to the amino terminal sequence lead to functional PCLs, whereas introduction of the amino acid sequence WRAAYKN (SEQ ID NO:19 (Bal112) causes total loss of phenylacetyl-CoA ligase activity.

2. Expression of the *Pseudomonas putida* U gene in the mold *Penicillium chrysogenum*

Once the pcl gene of *Pseudomonas putida* U had been characterized, the next objective was to introduce it into *Penicillium chrysogenum* with the aim of determining whether its expression in this mold resulted directly in the production of a greater quantity of penicillin G.

Figure 4:
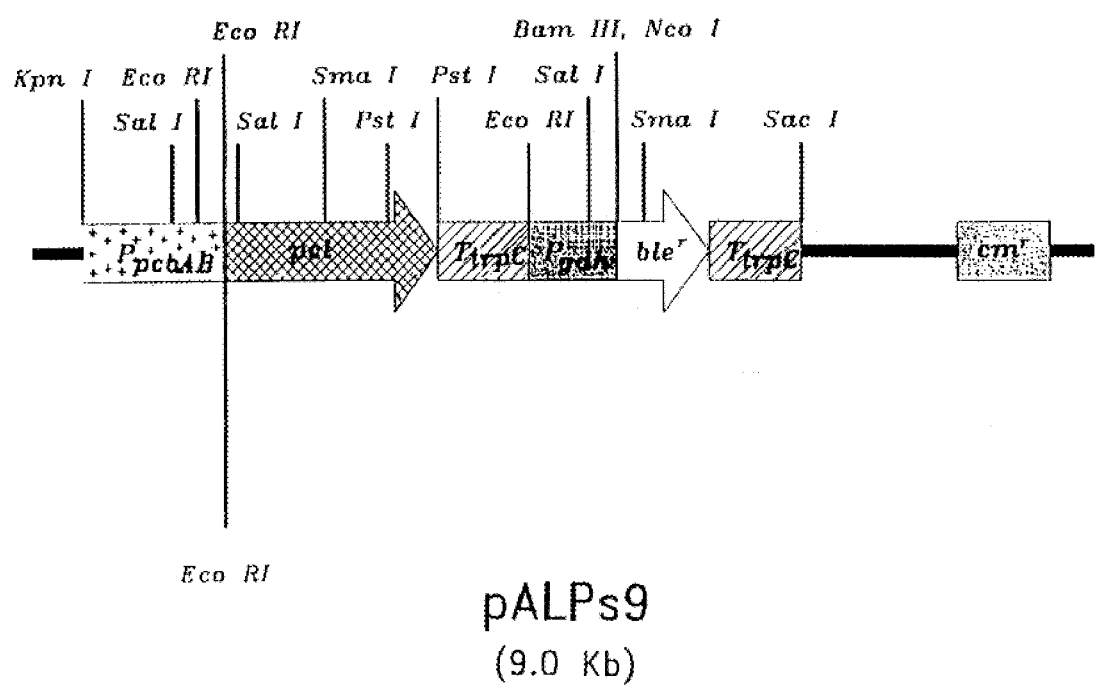

*Penicillium chrysogenum* Wis 54-1255 was chosen as the control strain. Usng the procedure described by Sanchez et al. (Ref. 17–18), protoplasts were obtained from mycelium that had grown in minimal medium. The protoplasts were transformed (17–18) with a plasmid derived from pBC (Stratagene), which contained a gene for resistance to the antibiotic phleomycin (Ref. 19), the promoter of the gene pcb AB, the ACVS of *Penicillium chrysogenum* (Ref. 19), the pcl gene of *Pseudomonas putida* U (starting from the construct indicated as Bal101) and the terminator of the trpC gene of *Penicillium chrysogenum*. The construct, called pALPs9 (FIG. 4), was produced as follows: A 1.2 Kb fragment NcoI, the ends of which were filled with Flenow (Ref. 13), was obtained from the plasmid pALP498, carrying a 2316 pb fragment BamHI which includes the bidirectional promoter pcbAB-pcbC (P pcbAB, see Ref. 19). This fragment was bound with Bal101, which had previously been digested with EcoRI, filled with Klenow and dephosphorylated, giving rise to insertions in both directions which were called pALPs1 and pALPs2. The clone pALPsI contains the pcl gene under the control of the promoter pcbAB. By digestion of this plasmid with XbaI, filling of the ends with Klenow and subsequent digestion with HindIII, a 2.8 Kb fragment with romo-HindIII ends was obtained which contained the pcbAB promoter-pcl gene complex. This fragment was subcloned in the fungal transformation vector pALfleo digested with XhoI, filled with Klenow and finally digested with HindIII. The plasmid obtained, which had the pcbAB promoter-pcl complex inserted in the same direction as the phleomycin resistance cassette (ble$^r$), was called pALPs8. Finally, a 725 pb fragment was introduced which includes the terminator of the trpC gene (TtrpC) of *Penicillium chrysogenum* in the EcoRV site of pALPs8, located between the pcl gene and the phleomycin resistance cassette. The construct bearing the trpC terminator, in the correct orientation, was called pALPs9 and used for expression of the pcl gene in different strains of *Penicillium chrysogenum*. This construct is shown in FIG. 4.

Figure 5:
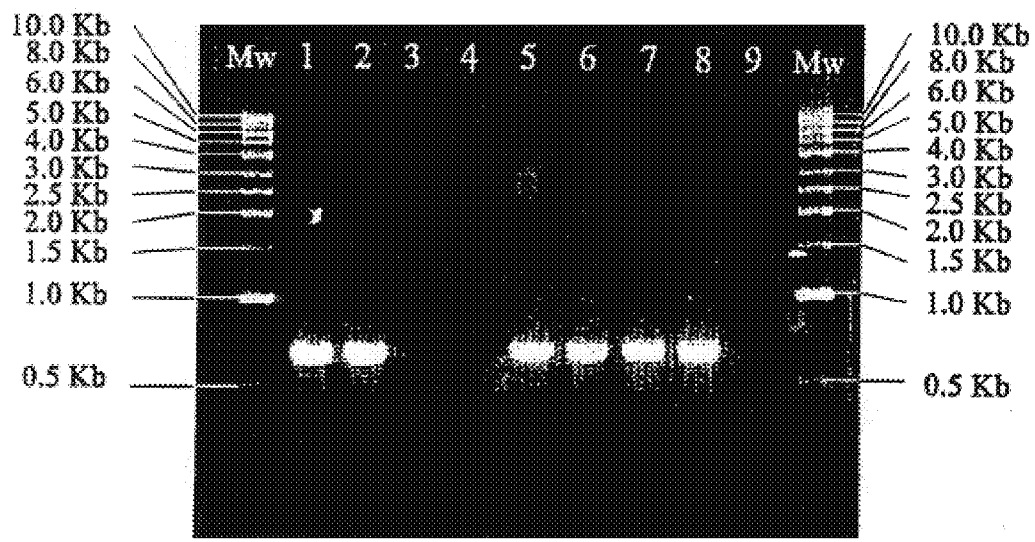

The transformant strains of *Penicillium chrysogenum*, which expressed the phleomycin resistance gene (ble$^r$), were selected (Ref. 19) and analyzed. All the transformants selected carried the pcl gene, as is shown by the fact that when amplification by PCR (polymerase chain reaction) was carried out, using the DNA of the different transformants and 2 internal oligonucleotides corresponding to the pcl gene, the respective sequences of which were: 5' D 3': ATC TGG GEC GGG AAC AC (SEQ ID NO:20) and GGC GCA AGG GEG ACA A (SEQ ID NO:21), amplified fragments of a size equivalent to that expected (651 base pairs) were obtained in all cases (FIG. 5). Amplification was not observed, however, either in the untransformed control strain or in that transformed with a construct in which the pcl gene had been eliminated (FIG. 5), which shows that (i) this same gene does not exist in the genome of *Penicillium chrysogenum* and (ii) there are not any similar sequences which could be amplified. 98% of the phleomycin-resistant transformants analyzed contained the pcl insert.

In order to complete this study, four transformants and an untransformed control were selected and both the expression of the gene (appearance of phenylacetyl-CoA ligase activity in cell-free extracts) and its effect on benzylpenicillin production were analyzed. For studies of this type the control and the transformants selected were inoculated in plates of complete production medium, the composition of which, in g/l, is as follows: corn steep solid 30, lactose 30, phenylacetic acid 1, agar 20 g and distilled water up to 1 l. The pH was adjusted to 6.5 with NaOH (30% w/v) and 10 g of CaCO$_3$ were then added. After it had been prepared, the medium was sterilized at 121° C. for 30 min and divided up at the rate of 30 ml per Petri dish of 9 cm diameter. The dishes were inoculated with the spores collected from the different colonies and were incubated at 25° C. for 9 days. At this point in time 10 ml of sterile H$_2$O per dish were added and the spores of each of the transformants were collected. These strains were used to inoculate an inoculation medium which contained, in corn steep solid 20, sucrose 20 and soluble maize distillates (DDS) 20. The pH of the medium was adjusted to 5.7 and 5 g of CaCO$_3$ were then added. The medium was distributed into 250-mi Erlenmeyer flasks containing 50 ml of the medium described. The flasks were sterilized in an autoclave at 121° C. for 30 min, and after cooling they were inoculated with 1 ml of a spore suspension containing $10^9$ spores/ml. The flasks were incubated at 25° C. in a Gallenkamp orbital shaker at 230 rpm for 24 h. 2.5-ml aliquots of this culture were then used to inoculate each 250-ml Erlenmeyer flask which contained 30 ml of complete production medium (without agar), prepared as described earlier. The fermentations were carried out for 56 h, taking aliquots at different times in order to determine the amount of penicillin produced, the dry weight (mg/ml) and the presence or absence of PCL in the different strains studied. The mycelium was collected by filtration, washed with 2000 volumes of sterile distilled $H_2O$ and dried with filter paper, and 1.5-g aliquots of wet mycelium (equivalent to 600 mg of dry weight) were resuspended in 0.5 M phosphate buffer solution, pH 8.0, containing 1 mM phenylmethylsulphonylfluoride (PMSF), and it was immediately disrupted by sonication. The extracts were centrifuged to eliminate the unbroken cells and the cell walls, and the supernatant was used to estimate phenylacetyl-CoA ligase activity. The procedure followed was the one employed for analysis of the enzyme in *Pseudomonas putida*, as we described earlier (see Ref. 9 and Spanish Patent P8902421). The formation of phenylacetyl-CoA (PA-CoA) was monitored by HPLC, using a high-pressure liquid chromatograph consisting of a Waters 600 pump, a Waters 481 detector, a 10 $\mu$m Nucleosil C18 column (250×4.6 mm), a Wisp 717 automatic injector and a Waters computer system (Millenium 2010). The injection volume was 50 $\mu$l. 0.2 M potassium phosphate, pH 4.5/isopropanol (90:10 vol/vol) was used as the mobile phase. The flow rate was 1 ml/min and the wavelength selected was 254 nm. Under these conditions PA-CoA has a retention time of 19.30 min and phenylacetic acid (PA) a retention time of 10.8 min. Analysis of the various transformants revealed that phenylacetyl-CoA ligase activity was detected in all of them, whereas this did not appear in the control (see Table II), which indicated that the pcl gene of *Pseudomonas putida* U was being expressed in *Penicillium chrysogenum*. The transformants thus obtained were deposited in the Spanish Standard Cultures Collection, where they were given the registration number CECT 20192.

The amount of penicillin G accumulated in the culture media was estimated by HPLC, using equipment consisting of a Waters 510 pump, a Varian 2050 detector, a 5-$\mu$m Hypersil ODS column (100×4.6 mm) and a Wisp 717 automatic injector. The injection volume was 20 $\mu$l. 0.05 M ammonium acetate, pH 6.8/methanol (60:40 vol/vol) was used as the mobile phase. The flow rate was 0.8 ml/min and the wavelength chosen was 235 nm. Under these conditions the retention time of penicillin G is 4.5 min. As can be seen in Table II, all the transformants produced between 84% and 121% more penicillin G than the control strain, which irrefutably demons-rates that the expression of the pcl of *Pseudomonas putida* I in *Penicillium chrysogenum* helps to increase penicillin G synthesis considerably in this mould.

BFIEF DESCRIPTION OF THE DRAWINGS

FIG. 1 Pathway for biosynthesis of penicillin G (benzylpenicillin) in *Penicillium chrysogenum*

Figure 2:
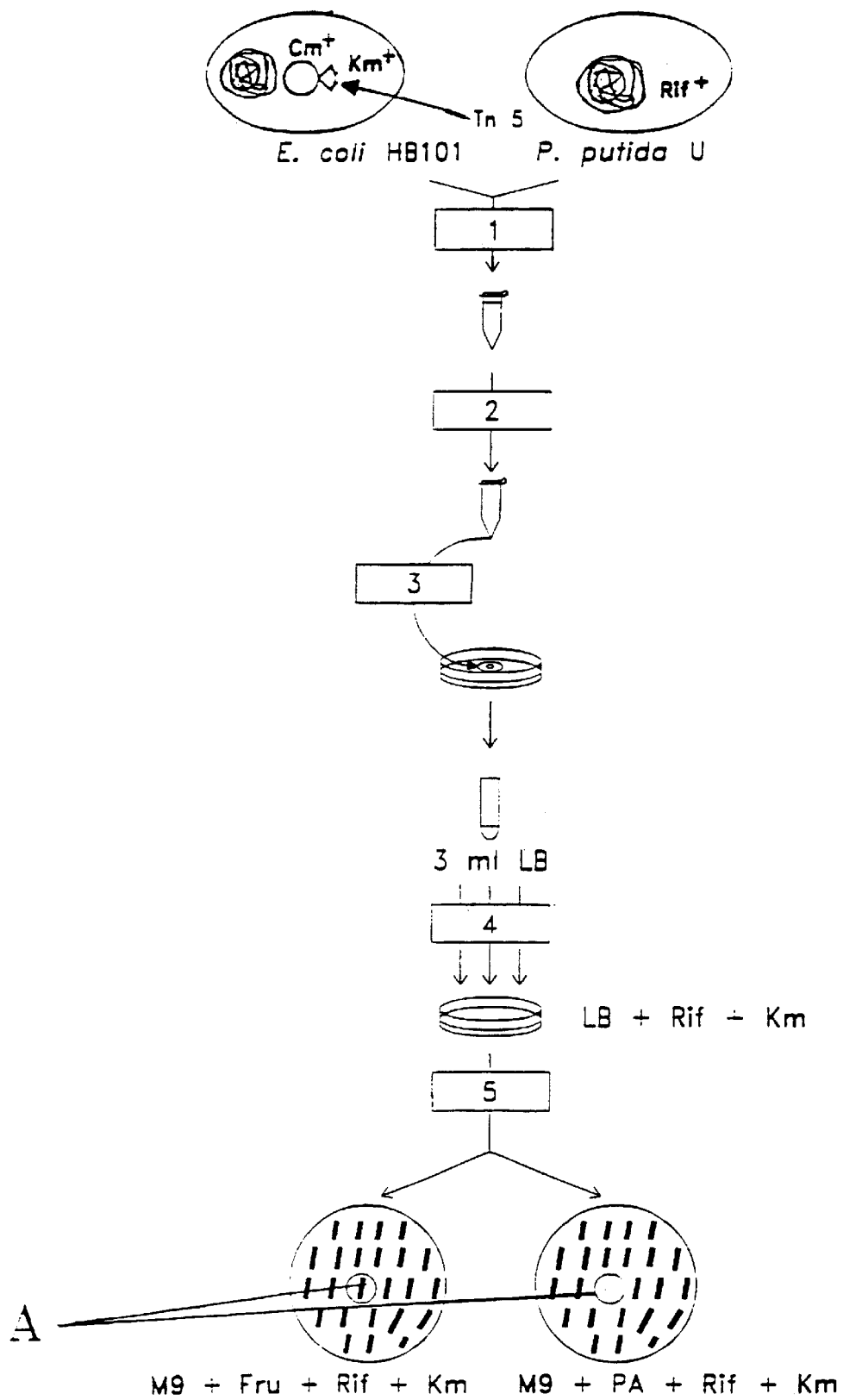

FIG. 2 Diagram of the protocol of mutagenesis with the transposon Tn5. Rif: rifampicin 20 $\mu$g/ml; Km: kanamycin 25 $\mu$g/ml; PA: phenylacetic acid; Fru: fructose; M9: minimal medium with a composition as described in Reference 13.

1 Mixing stage
2 Centrifugation for 3 min at 12000 rpm
3 Precipitate of *Escherichia coli+Pseudomonas putida*, 40 $\mu$l of which is collected and deposited in a filter on a dish with LB medium (Reference 13)
4 Dilution
5 Selection
A Mutants FIG. 3 pcl gene of intact Pseudomonas FIG. 4 pcl gene of Pseudomonas expressed under the control of the promoter of the pcbAB gene of *Penicillium chrysogenum*

FIG. 5 Amplification of part of the sequence of the pcl gene, using the oligonucleotides indicated in the report as initiators. (1) *Pseudomonas putida* U; (2) *Escherichia coli*+ pUC18+2090 pb insert (see report); (3) *Escherichia coli*+ pUC18 (without insert); (4) *Penicillium chrysogenum* Wis 54-1255 control; (5 to 8) Different CECT20192 transformants of *Penicillium chrysogenum* which contain the pcl gene in the construct pALPs9; (9) Transformants of *Penicillium chrysogenum* Wis 54-1255 containing a construct similar to pALPs9 without the pcl gene.

REFERENCES

1. Fawcett, P. and Abraham, E. P. (1975). In Methods in Enzymol. Ed., J. H. Hash, Vol. 43, pp. 471–473, Academic Press, New York.
2. Aharonowitz, Y.; Bergmayer, J., Cantoral, J. M., Cohen, G., Demain, A. L., Flnk, U., Kinghorn, J., Kleinkauf, H., MacCabe, A., Palissa, H., Pfeifer, E., Schweck, T., van Liempt, H., von Dohren, H., Wolfe, S., and Zhang, J. (1993). Bio/Technology 11:807–810.
3. Baldwin, J. E. and Bradley, M. (1990). Chem. Rev. 90:1079–1088.
4. Fernandez-Cañón, J. M., Reglero, A., Martinez-Blanco, H. and Luengo, J. M. (1989. J. Antibiotics 42:1398–1409.
5. Luengo, J. M. (1995), J. Antibiotics 48: 157–174.
6. Whiteman, P. A., Abraham, E. P., Baldwin, J. E., Fleming, M. D., Schofield, C. J., Sutherland, J. D. and Willis, A. C. (1990). FEBS Lett. 262, 342–344.
7. Barredo, J. L., Diez, B., Alvarez, E. and Martin, J. F. (1989). Curr. Genet 16:453–459.
8. Smith, D. J., Bull, J. H., Edward J. and Turner, G. (1989). Mol.Gen. Genet. 216:492–497.
9. Martinez-Blanco, H., Reglero, A., Rodriguez Aparicio, L. S. and Luengo, J. M. (1990). J. Biol. Chem. 265:7084–7090.
10. Martinez-Blanco, H., Reglero, A. and Luengo, J. M. (1991). J. Antibiotics 44:1252–1258.
11. Selvaraj, G. and Iyer, V. N. (1983). J. Bacteriol. 156:1292–1300.
12. Olivera, E. R., Reglero, A., Martinez-Blanco, H., Fernandez-Medarde, A., Moreno, M. A. and Luengo, J. M. (1994) Eur. J. Biochem. 221. 375–381.
13. Sambroock, J., Fritsch, E. F. and Maniatics, T. (1982). In "Molecular cloning, a Laboratory Manual". Cold Spring Harbor, N.Y.
14. Hori, K., Yamamoto, Y., Tokita, K., Saito, F., Kurotsu, T., Kanda, M., Okamura, K., Furuyama, J. and Saito, Y. (1991) J. Piochem. 110, 111–119.
15. Turgay, K., Krauze, M. and Marahiel, M. A. (199–2). Mol. Microbiol. 6, 529–546.
16. Henikoff, S. (1984). Gene, 28:351–359.
17. Sánchez, E., Rubio, V., Pefalva, M. A. and Perez-Aranda, A. (1987). European Patent Application 0235951B1.
18. Sánchez, E., Lozano, M., Rubio, V. and Peñalva, M. A. (1987). Gene 51, 97–102.
19. Diez, B., Gutiérrez, S., Barredo, J. L., van Solingen, P., van der Voort, L. H. M. and Martin, J. F. (1990). J. Biol.

Chem. 265:16358–16365.

TABLE I

| SEQUENCE | CLONE | PCL ACTIVITY |
|---|---|---|
| SEQ ID NO: 3 | BAL101 | YES |
| SEQ ID NO: 4 | BAL106 | YES |
| SEQ ID NO: 5 | BAL107 | YES |
| SEQ ID NO: 6 | BAL110 | NO |
| SEQ ID NO: 7 | BAL112 | YES |
| SEQ ID NO: 8 | BAL116 | YES |
| SEQ ID NO: 9 | BAL117 | YES |
| SEQ ID NO: 10 | BAL142 | YES |
| SEQ ID NO: 11 | BAL142 (pUC 18 mutant) | YES |

SEQUENCE LISTING

```
<160> NUMBER OF SEQ ID NOS: 21

<210> SEQ ID NO: 1
<211> LENGTH: 1401
<212> TYPE: DNA
<213> ORGANISM: Artificial Sequence
<220> FEATURE:
<223> OTHER INFORMATION: Description of Artificial Sequence:  The
      sequence is a fusion of a DNA sequence originating from pUC18 with
      another originating from Pseudomonas corresponding to the pcl
      gene.rdp
<221> NAME/KEY: CDS
<222> LOCATION: (67)..(1386)

<400> SEQUENCE: 1
catgacactc accgcgtggc ttgcaaccgc tggcgcgcgg cgtacaagaa caattcgagt      60 gaagcc atg aac atg tac cat gat gcc gac cgt gcc ctg ttg gac ccg       108
       Met Asn Met Tyr His Asp Ala Asp Arg Ala Leu Leu Asp Pro
         1               5                  10 atg gaa acc gcc agt gtc gac gcc ctg cgc cag cac cag ctg gag cgc      156
Met Glu Thr Ala Ser Val Asp Ala Leu Arg Gln His Gln Leu Glu Arg
 15                  20                  25                  30 ctg cgc tgg agc ctg aag cac gcc tac gac aat gtg ccg ctg tac cgc      204
Leu Arg Trp Ser Leu Lys His Ala Tyr Asp Asn Val Pro Leu Tyr Arg
                 35                  40                  45 cag cgc ttt gcc gaa tgc ggc gcc cac ccc gac gac ctc acg tgc ctg      252
Gln Arg Phe Ala Glu Cys Gly Ala His Pro Asp Asp Leu Thr Cys Leu
             50                  55                  60 gaa gac ctg gcg aag ttc ccc ttc acc ggc aag aac gac ctg cgc gac      300
Glu Asp Leu Ala Lys Phe Pro Phe Thr Gly Lys Asn Asp Leu Arg Asp
         65                  70                  75 aac tac ccc tac ggg atg ttc gcc gtc ccc cag gaa gag gtg gtg cgc      348
Asn Tyr Pro Tyr Gly Met Phe Ala Val Pro Gln Glu Glu Val Val Arg
     80                  85                  90 ctg cat gct tcc agc ggc acc acc ggc aag ccg acg gtg gtc ggt tac      396
Leu His Ala Ser Ser Gly Thr Thr Gly Lys Pro Thr Val Val Gly Tyr
 95                 100                 105                 110 acc cag aat gac atc aac acc tgg gcc aat gtc gtg gcg cgc tcg atc      444
Thr Gln Asn Asp Ile Asn Thr Trp Ala Asn Val Val Ala Arg Ser Ile
                115                 120                 125 cgt gcg gcc ggc ggg cgc aag ggt gac aaa gtg cat gtt tcc tac ggc      492
Arg Ala Ala Gly Gly Arg Lys Gly Asp Lys Val His Val Ser Tyr Gly
            130                 135                 140 tat ggg ctt ttc act ggc ggg ctt ggt cgg cac tac ggc gcc gag cgc      540
Tyr Gly Leu Phe Thr Gly Gly Leu Gly Arg His Tyr Gly Ala Glu Arg
        145                 150                 155
```

```
ctg ggc tgt acg gta atc ccg atg tcg ggt ggc cag acc gag aag cag      588
Leu Gly Cys Thr Val Ile Pro Met Ser Gly Gly Gln Thr Glu Lys Gln
    160                 165                 170 gtg cag ctg atc cgc gac ttt cag ccc gac atc atc atg gtc aca ccg      636
Val Gln Leu Ile Arg Asp Phe Gln Pro Asp Ile Ile Met Val Thr Pro
175                 180                 185                 190 tcc tac atg ctc aac ctg gcc gac gag atc gag cgc cag ggc atc gac      684
Ser Tyr Met Leu Asn Leu Ala Asp Glu Ile Glu Arg Gln Gly Ile Asp
                195                 200                 205 ccg cat gac ctc aag cta cgc ctg ggc att ttc ggt gcc gaa cct tgg      732
Pro His Asp Leu Lys Leu Arg Leu Gly Ile Phe Gly Ala Glu Pro Trp
            210                 215                 220 acc gat gaa cta cgt cgc tcg atc gag cag cgc ctg ggc atc aat gcc      780
Thr Asp Glu Leu Arg Arg Ser Ile Glu Gln Arg Leu Gly Ile Asn Ala
        225                 230                 235 ctc gac atc tat ggt ttg tcg gaa atc atg ggc ccc ggg gtg gcc atg      828
Leu Asp Ile Tyr Gly Leu Ser Glu Ile Met Gly Pro Gly Val Ala Met
    240                 245                 250 gaa tgc atc gaa acc aag gac ggc ccg acc ata tgg gaa gac cac ttc      876
Glu Cys Ile Glu Thr Lys Asp Gly Pro Thr Ile Trp Glu Asp His Phe
255                 260                 265                 270 tac ccc gaa atc atc gac ccg gtc acc ggc gaa gta ttg cca gac ggt      924
Tyr Pro Glu Ile Ile Asp Pro Val Thr Gly Glu Val Leu Pro Asp Gly
                275                 280                 285 cag ctg ggc gaa ctg gtg ttc acc tcg cta agc aaa gag gcg ctt ccg      972
Gln Leu Gly Glu Leu Val Phe Thr Ser Leu Ser Lys Glu Ala Leu Pro
            290                 295                 300 atg gtg cgc tac cgc acc cgt gac ctc acc cgc ctg ctg ccc ggc acc     1020
Met Val Arg Tyr Arg Thr Arg Asp Leu Thr Arg Leu Leu Pro Gly Thr
        305                 310                 315 gcc agg ccg atg cgg cgg atc ggc aag att acc ggg cgc agt gac gac     1068
Ala Arg Pro Met Arg Arg Ile Gly Lys Ile Thr Gly Arg Ser Asp Asp
    320                 325                 330 atg ctg atc att cgc ggc gtc aac gtg ttc ccg acc cag atc gag gaa     1116
Met Leu Ile Ile Arg Gly Val Asn Val Phe Pro Thr Gln Ile Glu Glu
335                 340                 345                 350 cag gta tta aaa ata aaa cag ctt tcc gag atg tat gag att cat ttg     1164
Gln Val Leu Lys Ile Lys Gln Leu Ser Glu Met Tyr Glu Ile His Leu
                355                 360                 365 tat cgc aat ggc aac ctg gac agc gta gag gtg cat gta gag ttg cgt     1212
Tyr Arg Asn Gly Asn Leu Asp Ser Val Glu Val His Val Glu Leu Arg
            370                 375                 380 gcg gag tgc cag cac ctc gat gaa ggc cag cgc aag ctg gtt atc ggg     1260
Ala Glu Cys Gln His Leu Asp Glu Gly Gln Arg Lys Leu Val Ile Gly
        385                 390                 395 gag ctg agc aaa cag atc aag acc tac atc ggc atc agc acc cag gtg     1308
Glu Leu Ser Lys Gln Ile Lys Thr Tyr Ile Gly Ile Ser Thr Gln Val
    400                 405                 410 cac ctg cag gct tgc ggc acg ctc aag cgt tcc gag ggc aag gcg tgc     1356
His Leu Gln Ala Cys Gly Thr Leu Lys Arg Ser Glu Gly Lys Ala Cys
415                 420                 425                 430 cac gtg tac gac aaa cgg ttg gcc agc tga ttcattcggc tgcct            1401
His Val Tyr Asp Lys Arg Leu Ala Ser
                435
```

<210> SEQ ID NO: 2
<211> LENGTH: 439
<212> TYPE: PRT
<213> ORGANISM: Pseudomonas

<400> SEQUENCE: 2

-continued

```
Met Asn Met Tyr His Asp Ala Asp Arg Ala Leu Leu Asp Pro Met Glu
 1               5                  10                  15
Thr Ala Ser Val Asp Ala Leu Arg Gln His Gln Leu Glu Arg Leu Arg
             20                  25                  30
Trp Ser Leu Lys His Ala Tyr Asp Asn Val Pro Leu Tyr Arg Gln Arg
         35                  40                  45
Phe Ala Glu Cys Gly Ala His Pro Asp Asp Leu Thr Cys Leu Glu Asp
     50                  55                  60
Leu Ala Lys Phe Pro Phe Thr Gly Lys Asn Asp Leu Arg Asp Asn Tyr
 65                  70                  75                  80
Pro Tyr Gly Met Phe Ala Val Pro Gln Glu Val Val Arg Leu His
                 85                  90                  95
Ala Ser Ser Gly Thr Thr Gly Lys Pro Thr Val Val Gly Tyr Thr Gln
             100                 105                 110
Asn Asp Ile Asn Thr Trp Ala Asn Val Val Ala Arg Ser Ile Arg Ala
         115                 120                 125
Ala Gly Gly Arg Lys Gly Asp Lys Val His Val Ser Tyr Gly Tyr Gly
     130                 135                 140
Leu Phe Thr Gly Gly Leu Gly Arg His Tyr Gly Ala Glu Arg Leu Gly
145                 150                 155                 160
Cys Thr Val Ile Pro Met Ser Gly Gly Gln Thr Glu Lys Gln Val Gln
                 165                 170                 175
Leu Ile Arg Asp Phe Gln Pro Asp Ile Ile Met Val Thr Pro Ser Tyr
             180                 185                 190
Met Leu Asn Leu Ala Asp Glu Ile Glu Arg Gln Gly Ile Asp Pro His
         195                 200                 205
Asp Leu Lys Leu Arg Leu Gly Ile Phe Gly Ala Glu Pro Trp Thr Asp
     210                 215                 220
Glu Leu Arg Arg Ser Ile Glu Gln Arg Leu Gly Ile Asn Ala Leu Asp
225                 230                 235                 240
Ile Tyr Gly Leu Ser Glu Ile Met Gly Pro Gly Val Ala Met Glu Cys
                 245                 250                 255
Ile Glu Thr Lys Asp Gly Pro Thr Ile Trp Glu Asp His Phe Tyr Pro
             260                 265                 270
Glu Ile Ile Asp Pro Val Thr Gly Glu Val Leu Pro Asp Gly Gln Leu
         275                 280                 285
Gly Glu Leu Val Phe Thr Ser Leu Ser Lys Glu Ala Leu Pro Met Val
     290                 295                 300
Arg Tyr Arg Thr Arg Asp Leu Thr Arg Leu Leu Pro Gly Thr Ala Arg
305                 310                 315                 320
Pro Met Arg Arg Ile Gly Lys Ile Thr Gly Arg Ser Asp Asp Met Leu
                 325                 330                 335
Ile Ile Arg Gly Val Asn Val Phe Pro Thr Gln Ile Glu Glu Gln Val
             340                 345                 350
Leu Lys Ile Lys Gln Leu Ser Glu Met Tyr Glu Ile His Leu Tyr Arg
         355                 360                 365
Asn Gly Asn Leu Asp Ser Val Glu Val His Val Glu Leu Arg Ala Glu
     370                 375                 380
Cys Gln His Leu Asp Glu Gly Gln Arg Lys Leu Val Ile Gly Glu Leu
385                 390                 395                 400
Ser Lys Gln Ile Lys Thr Tyr Ile Gly Ile Ser Thr Gln Val His Leu
                 405                 410                 415
```

Gln Ala Cys Gly Thr Leu Lys Arg Ser Glu Gly Lys Ala Cys His Val
            420                 425                 430

Tyr Asp Lys Arg Leu Ala Ser
        435

<210> SEQ ID NO: 3
<211> LENGTH: 30
<212> TYPE: DNA
<213> ORGANISM: Artificial Sequence
<220> FEATURE:
<223> OTHER INFORMATION: Description of Artificial Sequence: The
      sequence is a fusion of a DNA sequence originating from pUC18 with
      another originating from Pseudomonas corresponding to the pci
      gene.

<400> SEQUENCE: 3
atgaccatga ttacgaattc gagcgatgcc                                       30

<210> SEQ ID NO: 4
<211> LENGTH: 115
<212> TYPE: DNA
<213> ORGANISM: Artificial Sequence
<220> FEATURE:
<223> OTHER INFORMATION: Description of Artificial Sequence:  The
      sequence is a fusion of a DNA sequence originating from
      pUC18 with another originating from Pseudomonas
      corresponding to the pcl gene.

<400> SEQUENCE: 4
atgaccatga ttacgaattc gcagccgtat atgctgcgct catgacactc accgcgtggc       60
ttgcaaccgc tggcgcgcgg cgtacaagaa caattcgagt gaagccatga acatg           115

<210> SEQ ID NO: 5
<211> LENGTH: 91
<212> TYPE: DNA
<213> ORGANISM: Artificial Sequence
<220> FEATURE:
<223> OTHER INFORMATION: Description of Artificial Sequence:  The
      sequence is a fusion of a DNA sequence originating from
      pUC18 with another originating from Pseudomonas
      corresponding to the pcl gene.

<400> SEQUENCE: 5
atgaccatga ttacgaattc gagctcaccg cgtggcttgc aaccgctggc gcgcggcgta       60
caagaacaat tcgagtgaag ccatgaacat g                                     91

<210> SEQ ID NO: 6
<211> LENGTH: 75
<212> TYPE: DNA
<213> ORGANISM: Artificial Sequence
<220> FEATURE:
<223> OTHER INFORMATION: Description of Artificial Sequence:  The
      sequence is a fusion of a DNA sequence originating from
      pUC18 with another originating from Pseudomonas
      corresponding to the pcl gene.

<400> SEQUENCE: 6
atgaccatga ttacgaattc gagctggcgc gcggcgtaca agaacaattc gagtgaagcc       60
atgaacatgt accat                                                       75

<210> SEQ ID NO: 7
<211> LENGTH: 48
<212> TYPE: DNA
<213> ORGANISM: Artificial Sequence
<220> FEATURE:
<223> OTHER INFORMATION: Description of Artificial Sequence:  The sequence is a fusion of a DNA sequence originating from
pUC18 with another originating from Pseudomonas
corresponding to the plc gene.

<400> SEQUENCE: 7
atgaccatga ttacgaattc gagcaattcg agtgaagcca tgaacatg           48

<210> SEQ ID NO: 8
<211> LENGTH: 40
<212> TYPE: DNA
<213> ORGANISM: Artificial Sequence
<220> FEATURE:
<223> OTHER INFORMATION: Description of Artificial Sequence:  The
      sequence is a fusion of a DNA sequence originating from
      pUC18 with another originating from Pseudomonas
      corresponding to the pcl gene.

<400> SEQUENCE: 8
atgaccatga ttacgaattc gaggtgaagc catgaacatg                    40

<210> SEQ ID NO: 9
<211> LENGTH: 86
<212> TYPE: DNA
<213> ORGANISM: Artificial Sequence
<220> FEATURE:
<223> OTHER INFORMATION: Description of Artificial Sequence:  The
      sequence is a fusion of a DNA sequence originating from
      pUC18 with another originating from Pseudomonas
      corresponding to the pcl gene. hantoher

<400> SEQUENCE: 9
atgaccatga ttacgaattc caccgcgtgg cttgcaaccg ctggcgcgcg gcgtacaaga    60
acaattcgag tgaagccatg aacatg                                        86

<210> SEQ ID NO: 10
<211> LENGTH: 30
<212> TYPE: DNA
<213> ORGANISM: Artificial Sequence
<220> FEATURE:
<223> OTHER INFORMATION: Description of Artificial Sequence:  The
      sequence is a fusion of a DNA sequence originating from
      pUC18 with another originating from Pseudomonas
      corresponding to the pcl gene.

<400> SEQUENCE: 10
atgaccatga ttacgaattc gaggtaccat                               30

<210> SEQ ID NO: 11
<211> LENGTH: 29
<212> TYPE: DNA
<213> ORGANISM: Artificial Sequence
<220> FEATURE:
<223> OTHER INFORMATION: Description of Artificial Sequence:  The
      sequence is a fusion of a DNA sequence originating from
      pUC18 with another originating from Pseudomonas
      corresponding to the pcl gene

<400> SEQUENCE: 11
atgacatgat tacgaattcg aggtaccat                                29

<210> SEQ ID NO: 12
<211> LENGTH: 10
<212> TYPE: PRT
<213> ORGANISM: Artificial Sequence
<220> FEATURE:
<223> OTHER INFORMATION: Description of Artificial Sequence: The
      sequence is the peptide encoded by the DNA of SEQ ID NO: 11.

```
<400> SEQUENCE: 12

Met Thr Met Ile Thr Asn Ser Ser Asp Ala
  1               5                  10

<210> SEQ ID NO: 13
<211> LENGTH: 19
<212> TYPE: DNA
<213> ORGANISM: Artificial Sequence
<220> FEATURE:
<223> OTHER INFORMATION: Description of Artificial Sequence: The
      sequence is the same as the sequence at the ends of Tn5 transposon

<400> SEQUENCE: 13
acttgtgtat aagagtcag                                               19

<210> SEQ ID NO: 14
<211> LENGTH: 8
<212> TYPE: PRT
<213> ORGANISM: Artificial Sequence
<220> FEATURE:
<223> OTHER INFORMATION: Description of Artificial Sequence: The
      sequence is a consensus sequence corresponding to AMP binding site

<400> SEQUENCE: 14

Ser Ser Gly Thr Thr Gly Lys Pro
  1               5

<210> SEQ ID NO: 15
<211> LENGTH: 16
<212> TYPE: PRT
<213> ORGANISM: Artificial Sequence
<220> FEATURE:
<223> OTHER INFORMATION: Description of Artificial Sequence: The
      sequence corresponds to the sequence of phenylacetyl-CoA-ligase
      with a longer amino terminal end

<400> SEQUENCE: 15

Met Thr Met Ile Thr Asn Ser Ser Asn Ser Ser Glu Ala Met Asn Met
  1               5                  10                  15

<210> SEQ ID NO: 16
<211> LENGTH: 10
<212> TYPE: PRT
<213> ORGANISM: Artificial Sequence
<220> FEATURE:
<223> OTHER INFORMATION: Description of Artificial Sequence: The
      sequence corresponds to the sequence of pheylacetyl-CoA-ligase
      with a reduced amino terminal

<400> SEQUENCE: 16

Met Thr Met Ile Thr Asn Ser Arg Tyr His
  1               5                  10

<210> SEQ ID NO: 17
<211> LENGTH: 10
<212> TYPE: PRT
<213> ORGANISM: Artificial Sequence
<220> FEATURE:
<223> OTHER INFORMATION: Description of Artificial Sequence: The
      sequence corresponds to the sequence of pheylacetyl-CoA-ligase
      with a reduced amino terminal

<400> SEQUENCE: 17

Met Thr Met Ile Thr Asn Ser Ser Asp Ala
  1               5                  10

<210> SEQ ID NO: 18
```

```
<211> LENGTH: 25
<212> TYPE: PRT
<213> ORGANISM: Artificial Sequence
<220> FEATURE:
<223> OTHER INFORMATION: Description of Artificial Sequence:  The
      sequence comprises the amino terminal of the protein encoded by
      SEQ ID NO:6.

<400> SEQUENCE: 18

Met Thr Met Ile Thr Asn Ser Ser Trp Arg Ala Ala Tyr Lys Asn Asn
                 5                  10                  15

Ser Ser Glu Ala Met Asn Met Tyr His
             20                  25

<210> SEQ ID NO: 19
<211> LENGTH: 7
<212> TYPE: PRT
<213> ORGANISM: Artificial Sequence
<220> FEATURE:
<223> OTHER INFORMATION: Description of Artificial Sequence:  The
      sequence comprises the internal amino acid sequence of SEQ ID
      NO:18

<400> SEQUENCE: 19

Trp Arg Ala Ala Tyr Lys Asn
                 5

<210> SEQ ID NO: 20
<211> LENGTH: 17
<212> TYPE: DNA
<213> ORGANISM: Artificial Sequence
<220> FEATURE:
<223> OTHER INFORMATION: Description of Artificial Sequence:  The
      sequence is a primer for amplifying phenylacetyl-CoA-ligase gene

<400> SEQUENCE: 20
atctgggtcg ggaacac                                                17

<210> SEQ ID NO: 21
<211> LENGTH: 16
<212> TYPE: DNA
<213> ORGANISM: Artificial Sequence
<220> FEATURE:
<223> OTHER INFORMATION: Description of Artificial Sequence:  The
      sequence is a primer for amplifying pheylonetyl-CoA-ligase gene

<400> SEQUENCE: 21
ggcgcaaggg tgacaa                                                 16
```

What is claimed is:

1. An isolated DNA sequence comprising SEQ ID NO: 1, or a sequence hybridizing to the complement of SEQ ID NO: 1 under stringent conditions and encoding a phenylacetyl-CoA ligase.

2. An isolated DNA sequence according to claim 1, comprising SEQ ID NO:1.

3. An isolated DNA sequence according to claim 1, wherein the isolated DNA sequence encodes the amino acid of SEQ ID NO: 2.

4. A vector comprising the isolated DNA sequence of claim 1 operably linked to a promoter capable of directing expression of said isolated DNA in *Penicillium chrysogenum*.

5. A vector according to claim 4, wherein the promoter is from *Penicillium chrysogenum*.

6. A vector according to claim 4 which is plasmid.

7. A vector according to claim 6, wherein the plasmid is PALPs 9.

8. A transformed host organism comprising the vector of claim 4.

9. A transformed host organism according to claim 8, wherein the transformed host organism is a prokaryote selected from the group consisting of *E. coli* and an actinomycete.

10. A transformed host organism according to claim 8, wherein the transformed host organism is a eukaryote selected from the genus consisting of Penicillium, Aspergillus, Acremonium and Saccharomyces.

11. A transformed host organism according to claim 8, wherein the transformed host organism is selected from the group consisting of *Penicillium chrysogenum, Aspergillus nidulans, Acremonium chrysogenum* and *Saccharomyces cerevisiae*.

12. A transformed host organism according to claim 8, consisting of CECT20192 or a mutant or derivative thereof.

* * * * *